(12) United States Patent
Mitchell

(10) Patent No.: US 6,331,162 B1
(45) Date of Patent: Dec. 18, 2001

(54) PULSE WAVE VELOCITY MEASURING DEVICE

(76) Inventor: Gary F. Mitchell, 3 Draper Rd., Dover, MA (US) 02030

( * ) Notice: Subject to any disclaimer, the term of this patent is extended or adjusted under 35 U.S.C. 154(b) by 0 days.

(21) Appl. No.: 09/493,892

(22) Filed: Jan. 28, 2000

Related U.S. Application Data

(60) Provisional application No. 60/118,166, filed on Feb. 1, 1999.

(51) Int. Cl.[7] .................................................. A61B 5/00
(52) U.S. Cl. ........................ 600/485; 600/500; 600/507
(58) Field of Search ........................... 600/485, 500–503, 600/507

(56) References Cited

U.S. PATENT DOCUMENTS

| | | |
|---|---|---|
| 3,762,221 | 10/1973 | Coulthard . |
| 4,425,920 | 1/1984 | Bourland et al. . |
| 4,807,638 | 2/1989 | Sramek . |
| 5,101,828 | 4/1992 | Welkowitz et al. . |
| 5,140,990 | 8/1992 | Jones et al. . |
| 5,241,964 | 9/1993 | McQuilkin . |
| 5,265,011 | 11/1993 | O'Rourke . |
| 5,289,823 | 3/1994 | Eckerle . |
| 5,293,874 | 3/1994 | Takahashi et al. . |
| 5,301,675 | 4/1994 | Tomita . |
| 5,423,322 | 6/1995 | Clark et al. . |
| 5,535,747 | 7/1996 | Katakura . |
| 5,603,329 | 2/1997 | Hosaka et al. . |
| 5,671,750 | 9/1997 | Shinoda . |
| 5,743,856 | 4/1998 | Oka et al. . |
| 5,782,774 | 7/1998 | Shmulewitz . |
| 5,833,618 | 11/1998 | Caro et al. . |
| 5,865,755 | 2/1999 | Golub . |
| 5,865,758 | 2/1999 | Louzianine . |
| 5,921,936 | * 7/1999 | Inukai et al. ........................ 600/500 |
| 5,931,790 | * 8/1999 | Peel, III ............................. 600/500 |

OTHER PUBLICATIONS

G. F. Mitchell Et Al., A comparison of techniques for measuring pulse wave velocity in the rat, J App. Physiol., vol. 82, 1997, at 203–210.

G. F. Mitchell, Pulse pressure, arterial compliance and cardiovascular morbidity and motality, Curr. Opin, Nephrol. Hypertens., vol. 8, 1999, at 335–342.

* cited by examiner

Primary Examiner—Robert L. Nasser
(74) Attorney, Agent, or Firm—Holland & Bonzagni, P.C.; John A. Kramer, Esq.

(57) ABSTRACT

A pulse wave velocity measuring device generally comprises first and second photoplethysmographic transducers or probes electrically operably connected to a computer. The transducers are positioned on a patient's back to record pulse waveform information at two locations along the descending thoracic aorta. Additionally, the patient's ECG is recorded. Once the pulse waveforms and ECG waveform are recorded, noise or artifact ridden data is excluded, and the pulse waveforms are signal averaged using the ECG data points as fiducial references. Then, the signal averaged pulse waveforms are analyzed (again, with the ECG data providing fiducial points) to determine the foot of each waveform and the foot-to-foot transit time between the two transducers. Pulse wave velocity is then determined by dividing the distance between the transducers by the foot-to-foot transit time. Additionally, a mouthpiece pressure transducer and related circuitry can be connected to the computer for measuring a patient's pulse wave velocity as a function of blood pressure.

31 Claims, 7 Drawing Sheets

PULSE WAVE VELOCITY MEASURING DEVICE

This application claims priority from a Provisional Application, Ser. No. 60/118,166, filed Feb. 1, 1999.

FIELD OF THE INVENTION

The present invention relates to devices for analyzing blood flow in the human body, and, more particularly, to devices for measuring blood pulse wave velocity.

BACKGROUND OF THE INVENTION

Elevated blood pressure is an important cardiovascular risk factor. The commonly assessed components of blood pressure are systolic pressure and diastolic pressure, corresponding to the peak and trough of the blood pressure waveform, respectively. Recently, "pulse pressure," or the difference between peak and trough pressure, has also been shown to be an important cardiovascular risk factor. In fact, in some patient populations, it may be the most important measure of blood pressure.

The basis for this association is presumed to be increased stiffness of the aorta and large conduit blood vessels as a result of age, arteriosclerosis, and other factors. However, this association remains presumptive, in large part due to a limited ability to directly, accurately, and non-invasively measure aortic stiffness. Such reliable measurements are needed for directly establishing a relationship between vessel stiffness and cardiac events, and for evaluating the effects of new treatments aimed at reducing conduit vessel stiffness.

One reliable measure of vessel stiffness is the velocity at which a pressure or flow wave travels in the vessel, known as the "pulse wave velocity." It is currently difficult to non-invasively measure pulse wave velocity in the most highly compliant segment of the aorta that traverses the thorax and provides a substantial proportion of the buffering capacity of the arterial system. One major difficulty is the limited ability to obtain reliable pressure or flow waveform data from two sites within this segment of the aorta using minimal intervention. Another difficulty lies in accurately defining the distance and transit time between the recording sites.

One approach has been to record pressure or flow waveforms in the carotid and femoral arteries, which are located at opposite ends of the section of aorta in question. This technique suffers from two major difficulties. First, it is impossible to determine the appropriate transit between the two sites because there is parallel simultaneous transmission of the advancing wave up the carotid artery and down the aorta. Furthermore, the radically diverse properties of the entire aorta, carotid artery, iliac arteries, and femoral artery will influence the transit time, making it difficult to determine the specific properties of the highly compliant segment of the thoracic aorta. A related approach uses Doppler ultrasound to determine flow waveforms at the site of the left subclavian artery and the abdominal aorta. This technique suffers from parallel transmission in the subclavian region and from considerable susceptibility to parallax error at the site of transabdominal insonation of the aorta in the periumbilical region.

Echocardiography and magnetic resonance imaging have been utilized to obtain waveforms in the proximal and distal aorta. Both techniques have dual imaging/flow capability, making it possible to determine the location of measurement of the flow waveform. Echocardiography has excellent flow resolution, but does not allow for quantification of the complex, curvilinear distance between the measuring sites, which are generally taken in the ascending aorta and in the descending aorta near the diaphragm. Magnetic resonance imaging allows for precise quantification of this transit distance, but suffers from poor temporal resolution of the flow waveform. Combined, they provide for accurate yet cumbersome and extremely expensive measurement of pulse wave velocity.

A further difficulty encountered in attempting to evaluate changes in the intrinsic stiffness of the arterial wall through the measurement of pulse wave velocity lies in the dependence of arterial stiffness on distending pressure. The elasticity of the arterial wall is nonlinear, with stiffness increasing as distending pressure increases within the physiological range of blood pressure. As blood pressure may vary considerably in a patient during the day or during the stress associated with a visit to the physician's office, it is desirable to establish the pressure-corrected or pressure-independent pulse wave velocity as a measure of intrinsic arterial stiffness. It is possible to administer medications that acutely raise or lower the blood pressure to the desired range and then to measure pulse wave velocity at this target blood pressure. However, these medications may also alter the intrinsic stiffness of the artery through direct or indirect effects on the muscle layer within the arterial wall. Such an approach is also time consuming and carries a small but quantifiable risk to the patient.

Finally, a number of recently developed devices claim to evaluate total arterial compliance utilizing a variety of algorithms. Without discussing the limitations of these devices in too much detail, it suffices to note that total arterial compliance, to which these devices relate, is not the same as proximal aortic stiffness, to which the present invention relates.

Accordingly, it is a primary object of the present invention to provide a method and device for accurately and safely determining the pulse wave velocity of blood in a blood vessel.

A more specific object is to provide a method and device for non-invasively measuring the pulse wave velocity of blood in the descending thoracic aorta.

Another object of the present invention is to provide a method and device for evaluating the pressure dependence of pulse wave velocity of blood in a blood vessel.

Yet another object of the present invention is to provide a pulse wave velocity measurement method and device that allows for easy and accurate determination of the distance between vessel measurement sites.

Still another object is to provide a method and device for determining a pressure-independent pulse wave velocity as a measure of intrinsic arterial stiffness.

SUMMARY OF THE INVENTION

An improved pulse wave velocity ("PWV") measuring device is disclosed for analyzing blood flow in the human body. In a preferred embodiment, the PWV measuring device generally comprises first and second photoplethysmographic ("PPG") transducers or probes electrically connected to a computer via PPG amplifiers. The transducers are positioned on a patient's back to record pulse waveform information at two locations along the descending thoracic aorta. Additionally, the patient's electrocardiograph ("ECG") is recorded.

Once the PPG pulse waveforms and ECG waveform are recorded, noise or artifact ridden data is excluded (manually or automatically), and the two pulse waveforms are signal averaged using the ECG data points as fiducial references to increase the pulse waveforms' signal-to-noise ratio. Then, the signal averaged PPG waveforms are analyzed (again, with the ECG data providing fiducial points) to determine the foot of each waveform and the foot-to-foot transit time between the two PPG transducers. Pulse wave velocity is then determined by dividing the distance between the transducers by the foot-to-foot transit time.

Additionally, a mouthpiece pressure transducer and related circuitry can be connected to the computer for measuring a patient's pulse wave velocity as a function of blood pressure. The patient exerts stepped respiratory force (positive and negative) on the mouthpiece, with the PWV being recorded each time. This information is correlated to the patient's at-rest mean blood pressure, establishing a relationship that can be used to predict blood pressure by measuring a patient's pulse wave velocity.

BRIEF DESCRIPTION OF THE DRAWINGS

These and other features, aspects, and advantages of the present invention will become better understood with respect to the following description, appended claims, and accompanying drawings, in which:

DETAILED DESCRIPTION OF THE PREFERRED EMBODIMENTS

Figure 1:
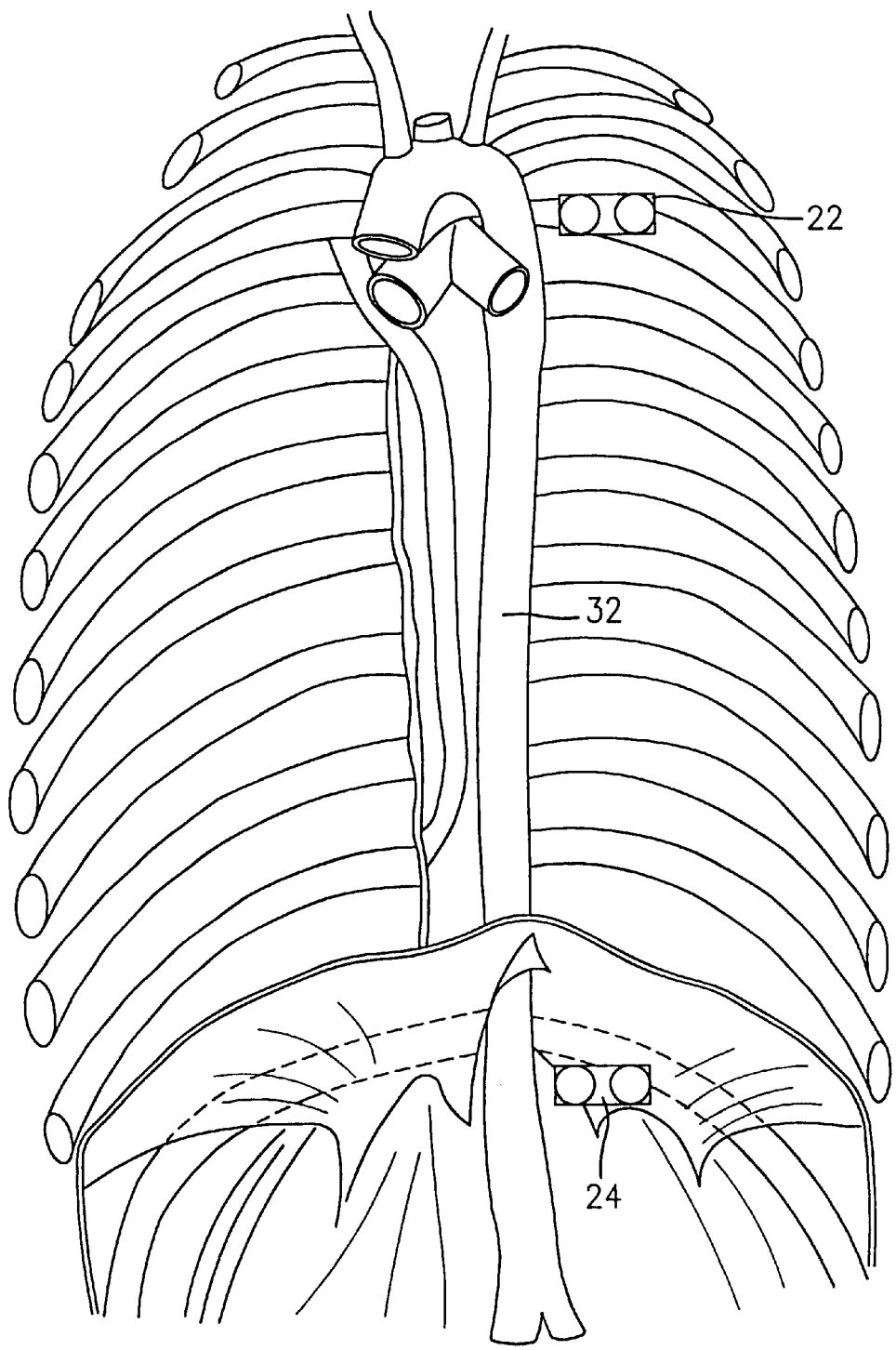
FIG. 1 is an anatomical view of the human torso showing preferred placement locations for a pair of transducers, according to the present invention.

Turning now to FIGS. 1–7B, a preferred embodiment of a pulse wave velocity ("PWV") measuring device 20, according to the present invention, will now be given. The PWV measuring device 20 generally comprises proximal and distal photoplethysmographic ("PPG") transducers or probes 22, 24 electrically connected to a computer 26 via PPG amplifiers 28, 30. The transducers 22, 24 are positioned on a patient's back to effectively record a pulse waveform at two locations along the descending thoracic aorta 32. Additionally, the patient's electrocardiograph ("ECG") is recorded via standard ECG leads 34 also attached to the patient. The signal outputs of the transducers 22, 24 and ECG leads 34 are analyzed according to an algorithm that uses the signal outputs to determine the time between pulse waves arriving at the proximal transducer 22 and at the distal transducer 24. With a known distance between the two transducers 22, 24, the pulse wave velocity can be calculated.

The PWV measuring device 20 evaluates pulse wave velocity along a straight segment of the descending thoracic aorta 32, making measurement of the transit distance straightforward when properly undertaken. The device 20 obtains a flow pressure or diameter waveform at two sites along this segment using one of a number of means, including, but not limited to, Doppler ultrasound, PPG, impedance plethysmography, or laser Doppler.

The preferred embodiment of the present invention uses PPG because the technology is easy to implement and is relatively inexpensive. The principals of photoplethysmography are well known to those skilled in the art of noninvasive hemodynamic monitoring. Each of the PPG probes 22, 24 consists of one or more infrared light transmitters and an infrared light sensing element. Infrared light is transmitted into the skin and is reflected back from various structures under the skin and is detected by the light sensor. The blood in vessels beneath the skin absorbs a portion of the infrared light. The pressure varies within these vessels with each beat of the heart. The increase in pressure following a heart contraction distends the vessels with additional blood, resulting in additional absorption of infrared light. Thus, the amount of light detected by the sensor changes rhythmically with the cardiac cycle, producing a waveform that closely resembles the pressure waveform within the vessels.

Figure 2:
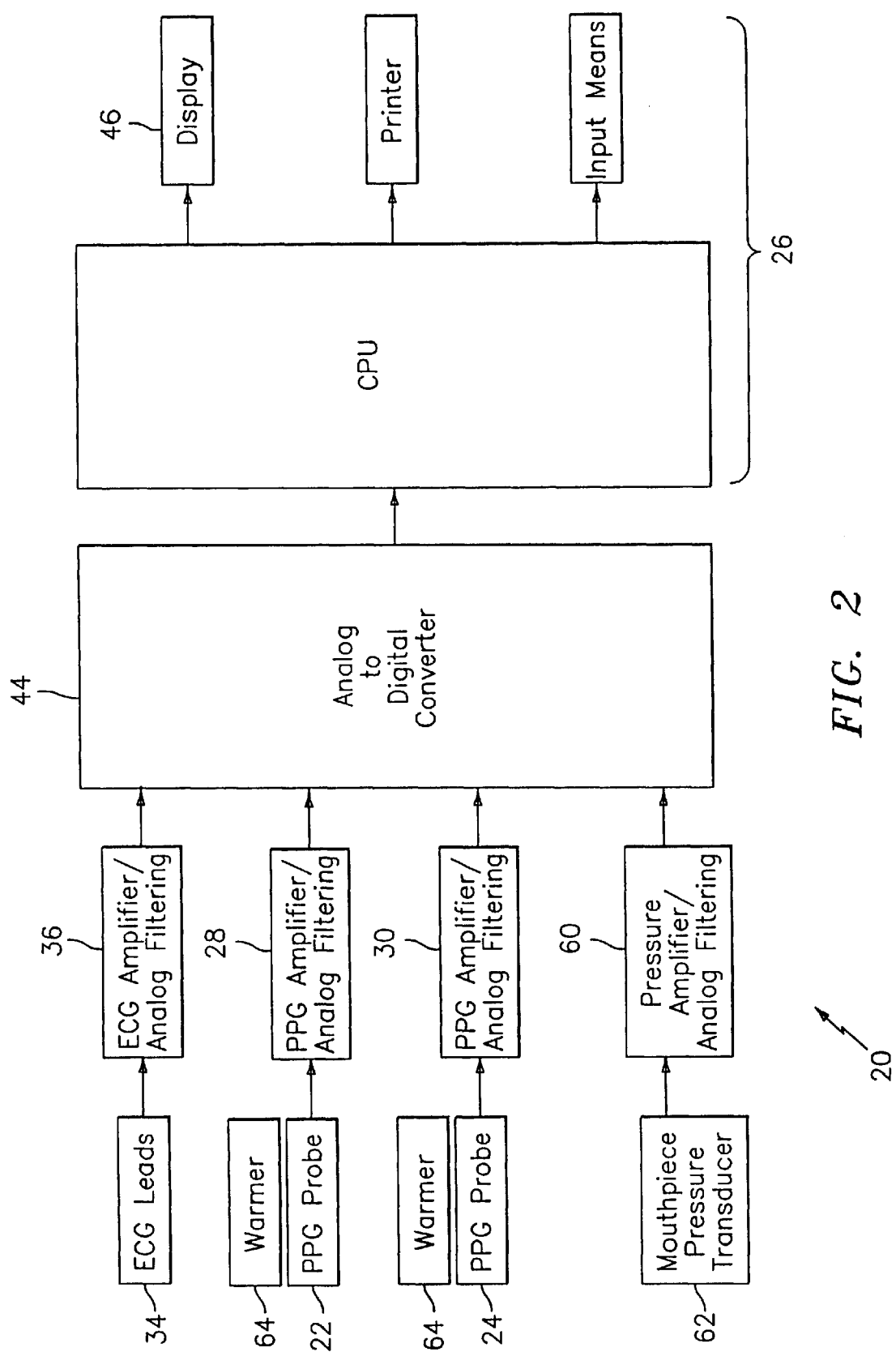
FIG. 2 is a schematic diagram of a pulse wave velocity measuring device constructed in accordance with the present invention.

The preferred embodiment of the present invention takes advantage of the uniform and symmetrical distribution of intercostal vessels that branch off from the thoracic aorta 32 and supply blood to the skin and tissues overlying this segment of aorta (see FIG. 1). From the level of the fourth thoracic vertebra through to the lumbar region, the intercostal arteries take off from the aorta at a consistent angle and immediately supply blood to the surrounding tissue overlying that segment of the aorta. The timing of the arrival of the advancing pressure waveform at a given level in the aorta can therefore be assessed by using PPG to measure blood flow in the superficial tissue overlying the spine at that level. This approach is employed at two or more sites along the aorta simultaneously, as indicated in FIGS. 1 and 2. Transit of the waveform through the intercostal artery and smaller vessels does delay detection of the foot of the waveform at a given site within the aorta. However, this delay is present and uniform at each of the measuring sites and therefore cancels out when the relative time of arrival at the various sites is determined.

It is important to note that this embodiment of the invention requires that the acquisition sites fall between approximately the fourth thoracic and the second lumbar vertebra, e.g., as shown in approximation in FIG. 1. During the procedure, the locations of these vertebra are readily determined by a physician or technician trained in the proper use of the invention. Furthermore, the PPG transducers 22, 24 must be applied with a constant relationship to the location of the vertebral process at each site along the spine, being placed at the level of the spinous process and either directly overlying or just to the left of the spinous process. Also, the frequency response and sensitivity of the PPG probes and circuitry must be carefully balanced in order to avoid introducing a transit time bias between channels.

As mentioned above, the PWV measuring device 20 includes an ECG monitoring channel comprising the ECG leads 34 (which are attached to a patient in a conventional fashion) and a standard ECG amplifier/filter 36.

Figure 3:
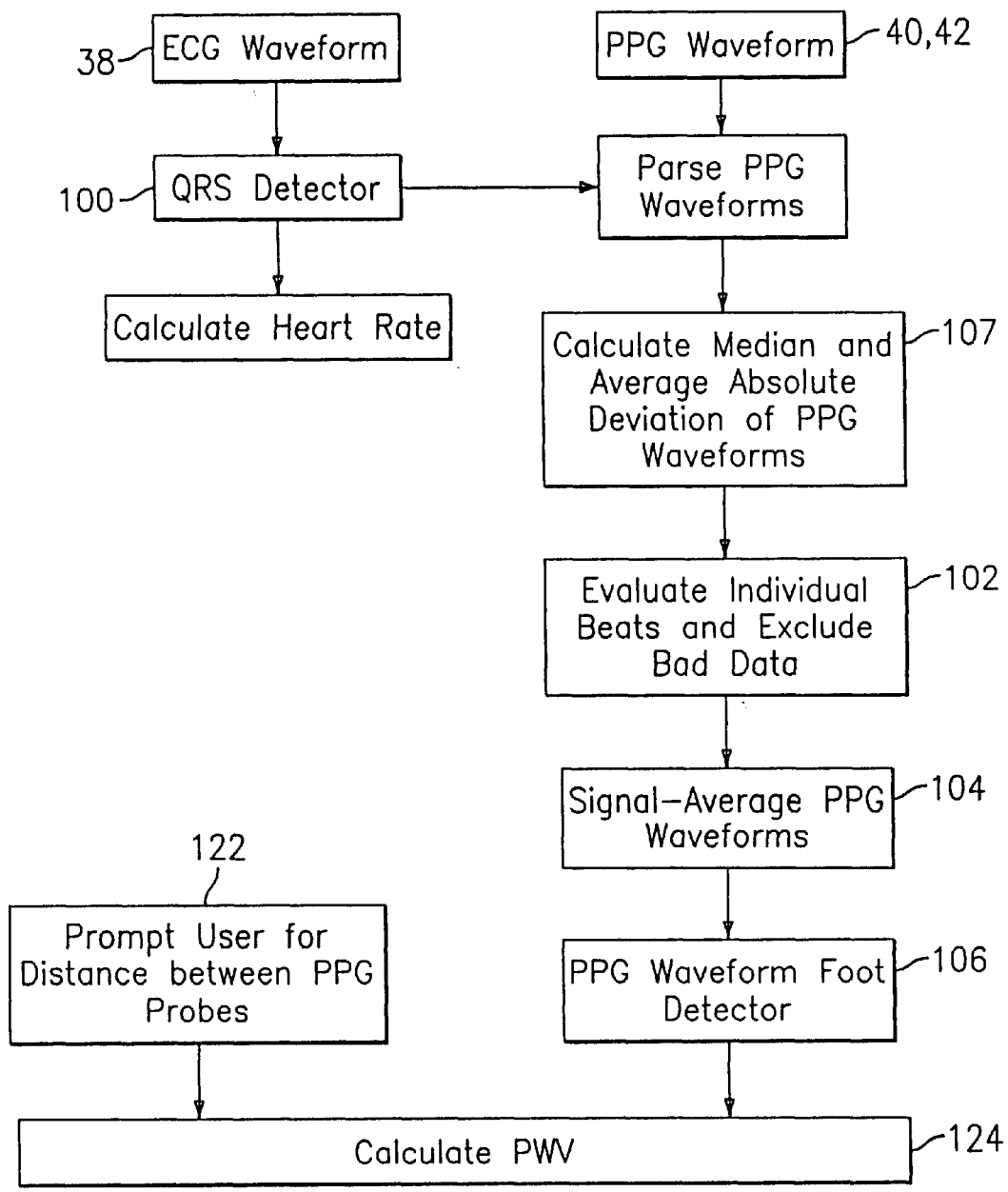
FIG. 3 is a flow diagram of a waveform analysis algorithm according to the present invention.
Figure 4:
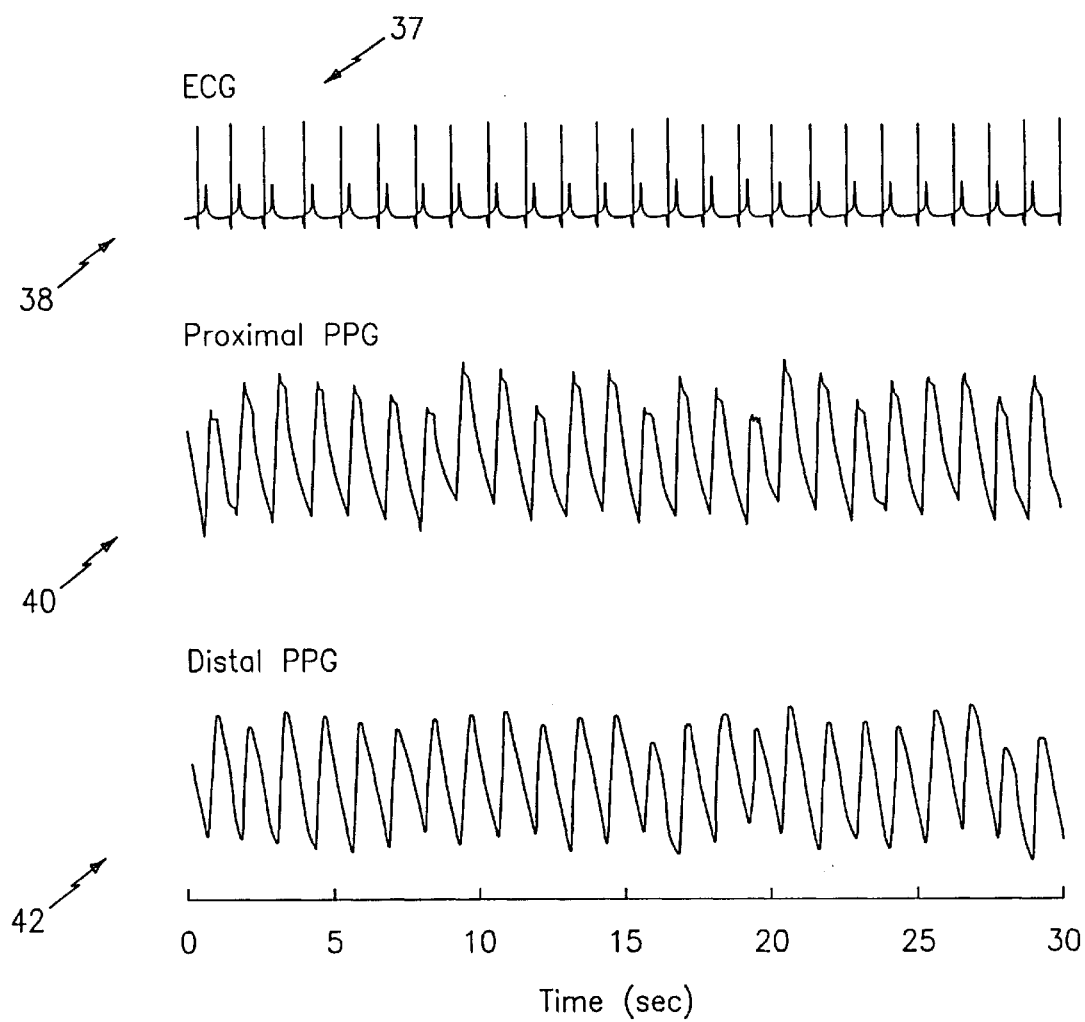
FIG. 4 is a schematic view of thirty seconds of raw ECG and proximal and distal PPG waveform data.
Figure 5:
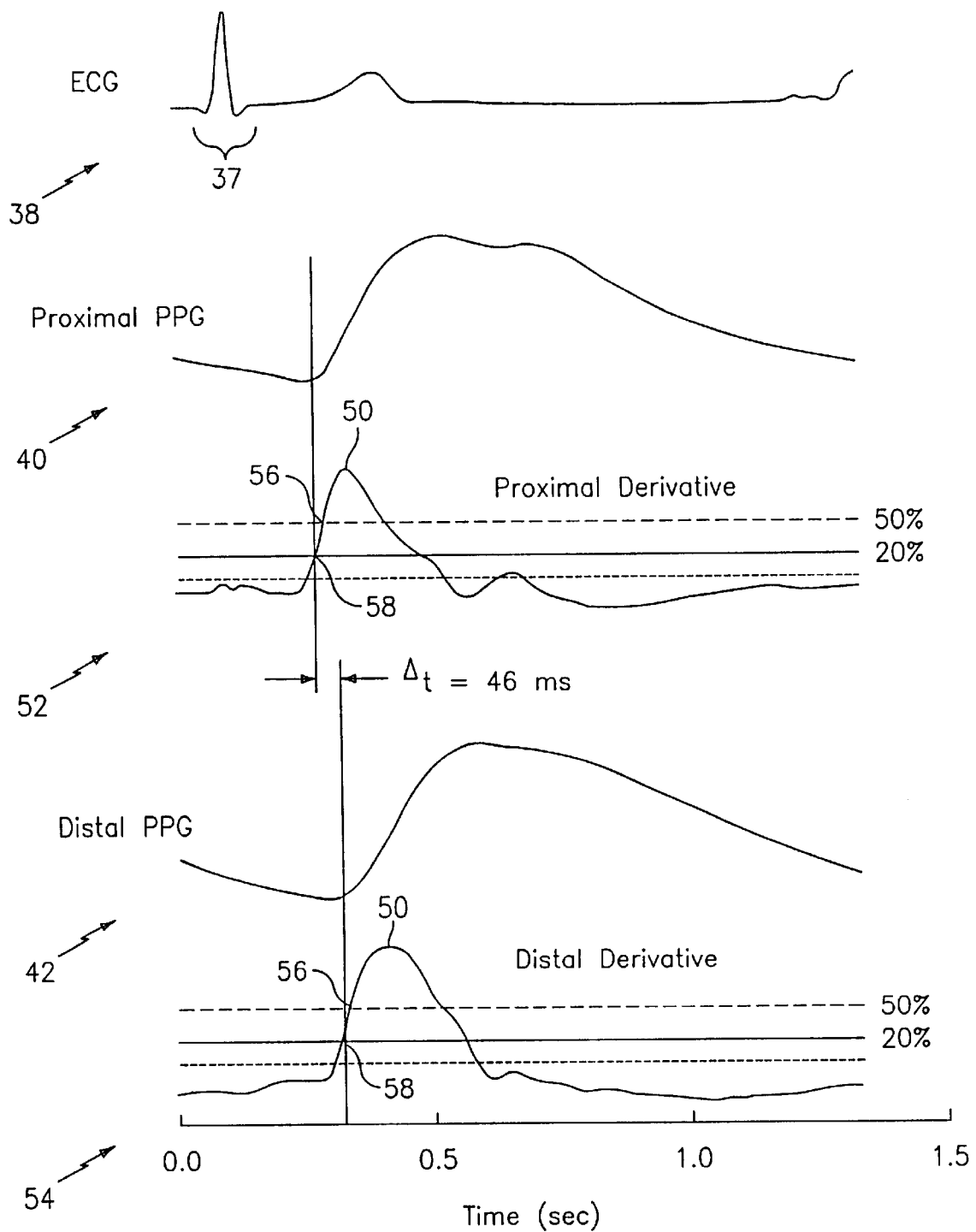
FIG. 5 is a schematic view of the signal-averaged ECG and PPG waveforms along with graphs of the derivative waveforms showing the preliminary 50% threshold and the final 20% threshold employed in locating the foot of the PPG waveforms.

Turning now to FIG. 3 (Step 100), the measuring device 20 detects the peak of a "QRS complex" 37 of an ECG signal 38 (see FIGS. 4 and 5; also, for a brief explanation of the cardiac cycle in general, see U.S. Pat. No. 6,006,131 to Cooper, et al.) The device 20 uses this as a fiducial point for averaging the proximal and distal waveforms 40, 42 (e.g., the signal waveforms obtained from the PPG transducers 22, 24) to improve the signal-to-noise ratio of the waveforms. Data is acquired for thirty seconds, during which time the patient should remain still, breathe quietly and not talk. More specifically, the ECG leads 34 transfer the ECG signal 38 to the ECG amplifier 36. The amplified ECG signal 38 is passed from the ECG amplifier 36 to an analog-to-digital converter 44, which acts as an interface with the computer 26 for converting the analog signals 38, 40, 42 (from the ECG leads 34 or the PPG probes 22, 24) to a digital form useable by the computer 26. It should be noted that the A-D converter 44 can be part of the computer 26. An operator continuously evaluates the waveforms on a computer monitor 46 and looks for artifacts produced by the patient moving, talking, coughing or the like. Once thirty seconds of clean data have been obtained, the operator terminates data acquisition and may review the data and reject any cardiac cycles with obvious noise or artifacts (Step 102). Once waveforms are accepted, the device 20 signal averages the proximal and distal waveforms 40, 42 (Step 104), using the peak of the QRS 37 as the fiducial point, and then establishes the difference in arrival time between the two sites (Step 106), and as further discussed below.

To enhance the reliability of the measurements, morphological screening of waveforms may be used as a basis for excluding waveforms from the signal-averaged composite wave. Qualification of waveforms may be purely statistical or may be based on predetermined or user-specified criteria for an acceptable waveform morphology using measures of rise time and rate, time to waveform peak, systolic ejection period, and the like. As an example, as shown in FIG. 3, in the preferred embodiment of the device 20, a first-pass analysis of the waveforms involves calculating the median value at each point on the putative signal-averaged waveforms (Step 107). The average absolute deviation from the median at each point is also determined. This median waveform and the variance at each point is then used as a criterion for excluding waveforms contaminated by artifacts, such as respiratory variation or movement. Such waveforms are defined as those waveforms wherein 20% or more of the waveform points fall outside the confidence intervals established by the median plus or minus three times the average deviation at each point. Once contaminated waveforms have been excluded, the median waveforms of the proximal and distal recordings are again computed and the proximal median waveform is compared to the distal median waveform in order to ensure that both channels have acquired a valid tracing. This comparison is achieved by performing a time domain cross correlation of the waveforms. The cross correlation is performed by assessing the correlation coefficient (Pearson's R) between proximal ($x_i$) and distal ($y_i$) waveforms. The R value is assessed 100 times as the distal waveform is shifted in one ms increments up to 100 ms earlier. If the maximum correlation coefficient is <0.90, the device returns an error code and does not compute a PWV. Once these quality control measures have been performed and passed, waveforms that meet the inclusion criteria are signal averaged using the standard arithmetical mean at each point. These signal-averaged waveforms are then passed to the transit time detection algorithm for determination of the pulse wave transit time.

Another important feature of the device 20 is the method used by the transit time detection algorithm to determine the transit time between the signal-averaged waveforms (Step 106). Due to the presence of reflected waves in the arterial system, pressure waveform morphology changes considerably along even relatively short distances in the thoracic aorta 32. As a result, standard time-difference-of-arrival techniques, such as cross-correlation (as implemented in U.S. Pat. No. 5,535,747 to Katakura) or phase-slope and impulse-response techniques (as described in Mitchell et al., A Comparison of Techniques for Measuring Pulse Wave Velocity in the Rat, J. Appl. Physiol. 82, 203–210 (1997)), are not applicable. Rather, it is necessary to reliably define the foot of the advancing pressure waveform, which is unaffected by the presence of reflected waves, and then to establish the foot-to-foot transit times between measurement sites with accuracy at the millisecond level or better. To achieve this temporal resolution, waveforms must be digitized at a sampling rate of at least 1000 Hz in a digital implementation of the invention. Furthermore, the front-end analog circuitry of the PPG amplifiers/filters 28, 30 must have a low pass corner (3 dB) frequency of at least 20 Hz or greater in order to minimize distortion of the sharp transition at the waveform foot. However, 60 Hz contamination of the signal must be avoided as this may bias the location of the detected foot of the waveform.

Figure 6:
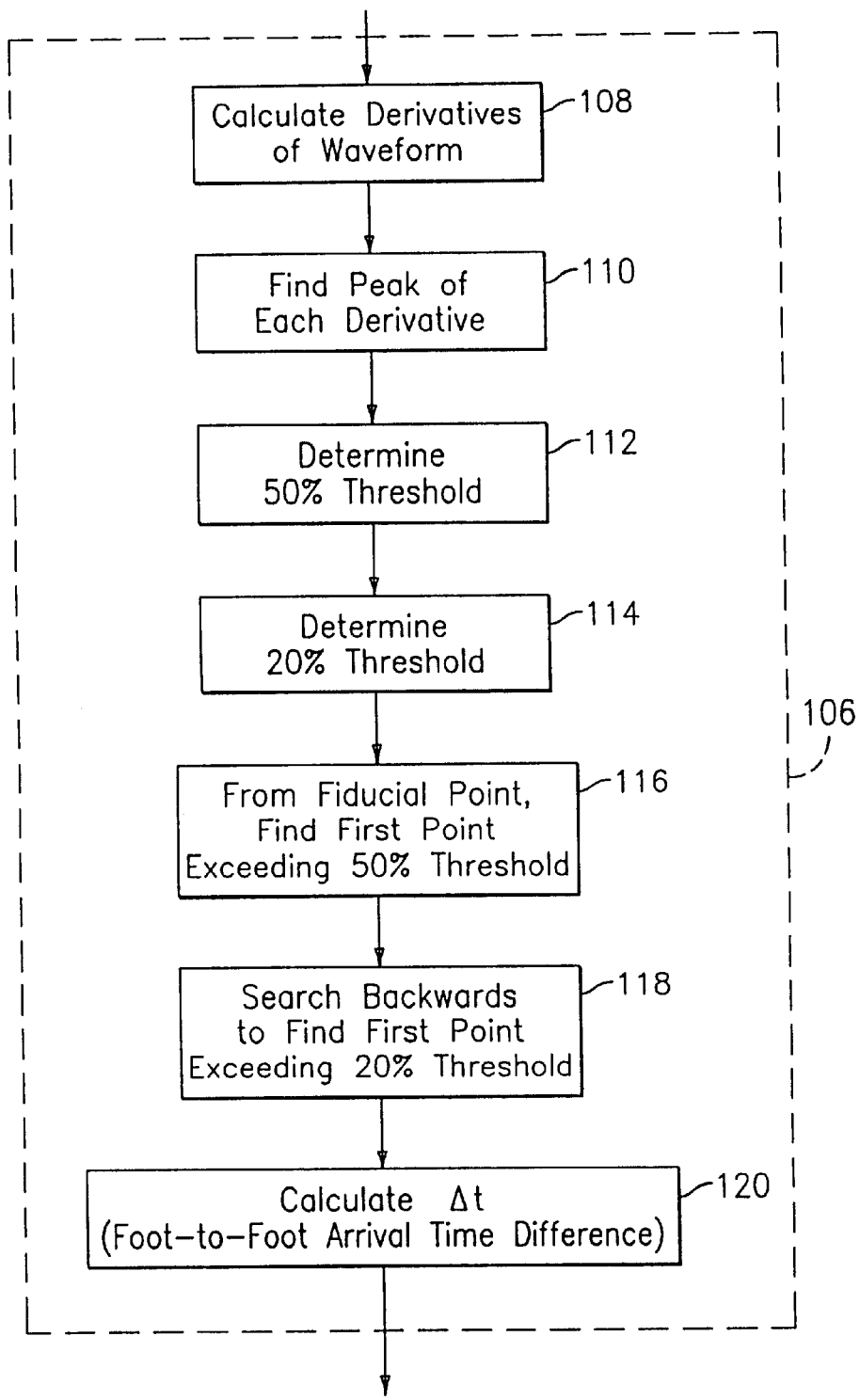
FIG. 6 is a flow diagram of a waveform foot-to-foot transit time algorithm according to the present invention.

Turning now to FIGS. 5 and 6, an adaptive, derivative-based algorithm is used to establish the foot-to-foot transit time between the two PPG waveforms 40, 42 (Step 106). First, after the waveforms are obtained (Step 104), a derivative 52, 54 of each waveform 40, 42 is calculated (Step 108). A peak 50 of the derivative 52, 54 of each waveform 40, 42 is then located and quantified (Step 110). Next, a preliminary threshold is then set equal to 50% of the peak derivative value (Step 112), and a final threshold is set equal to 20% of the peak derivative value (Step 114). Next, searching forward from the fiducial point (the peak of the QRS complex 37), the algorithm determines the location 56 of the first point in the derivative waveform that exceeds the preliminary (50%) threshold (Step 116). From this point 56, searching backwards, the algorithm identifies the last point 58 on the derivative waveform that exceeds the final (20%) threshold (Step 118). This point represents a robust estimate of the foot of the waveform. This procedure is carried out independently on the proximal and distal waveforms 40, 42, using thresholds determined by the peak derivative of the waveform being analyzed. This approach adapts the threshold to changes in waveform morphology as the pressure wave propagates distally.

Those with ordinary skill in the art will appreciate that this approach to analyzing waveforms may be carried out without use of an ECG channel. For example, the proximal signal 40 could be used to establish a fiducial point for signal averaging both the proximal and distal waveforms 40, 42. Such an approach would modestly simplify the circuitry and difficulty of performing the test. However, the QRS 37 provides a precise, clean fiducial point for signal averaging and thereby improves signal-to-noise ratio. For example, if noise contaminates the proximal waveform 40, such noise may also influence the detection of the foot of the waveform. In this case, signal averaging of the waveform with respect to the so detected foot of the waveform will not improve the signal-to-noise ratio with respect to this contamination signal. Thus, the bias in foot location will persist in the signal-averaged waveform. If similar contamination, e.g., 60 Hz noise from electrical mains, is present in the distal waveform 42, it too will persist after averaging and will potentially have an adverse effect on the measured transit time.

As an alternative to signal averaging the waveforms and analyzing the averaged waveforms, it is also possible to eliminate the ECG channel and to analyze waveform pairs on a beat-by-beat basis. To enhance the reliability of the measurement, recordings may be taken until the beat-to-beat variability in the transit time, _t, between the proximal and distal waveforms falls within a predetermined or user-specified tolerance, e.g., 5% of the mean. Furthermore, waveform pairs with a transit time that deviates significantly from the central tendency (mean or median) may be identified and omitted from the analysis in order to enhance the reliability of the estimate of pulse wave velocity. Such outliers may be identified by considering their deviation from the central value for transit time or by assessing proximal and distal waveform morphology prior to determining transit time. This latter morphological screening of waveforms is similar to the procedure described above for excluding waveforms from the signal-averaged composite wave. Waveform pairs wherein either the proximal or distal waveform fails to meet these inclusion criteria would then be excluded from the analysis.

Turning back to FIGS. 3, 5 and 6, once the proximal and distal PPG waveforms 40, 42 have been analyzed according to any of the aforementioned means, the transit time, _t, is calculated by taking the foot-to-foot difference between the distal and the proximal arrival times (Step 120), e.g., the time difference between the 20% threshold points 58 of the derivative waveforms 52, 54, as shown in FIG. 5. The measured distance between the transducers, _s, a value that is entered into the computer 26 by the user (Step 122), is divided by the transit time (Step 124) to give the pulse wave velocity (PWV) of the vessel segment in question:

$$PWV=\_s/\_t \qquad \text{Eq. 1.}$$

As an alternative to the two-site method described in the preferred embodiment of the device, multiple segments, i.e., three or more, corresponding to different levels of the thoracic spine, may be assessed in order to minimize the effects of variability in vascular structure at a given level. This approach may be achieved by sequentially performing multiple measurements at various levels using a single waveform sensor in conjunction with a simultaneous ECG for use as a fiducial point, or by employing a system with a plurality of waveform sensors and circuits, allowing measurement at multiple sites along the aorta simultaneously. Regardless of the methodology employed to obtain multiple measurements at various sites along the aorta, it should be apparent that computation of pulse wave velocity in this embodiment of the device will be best achieved by linear regression analysis of the data. The slope of the linear relationship between transit time to each site (abscissa) versus the distance to that site from the most proximal site of measurement (ordinate) would be the average pulse wave velocity along the segment of aorta between the most proximal and most distal measurement sites.

Figure 7A:
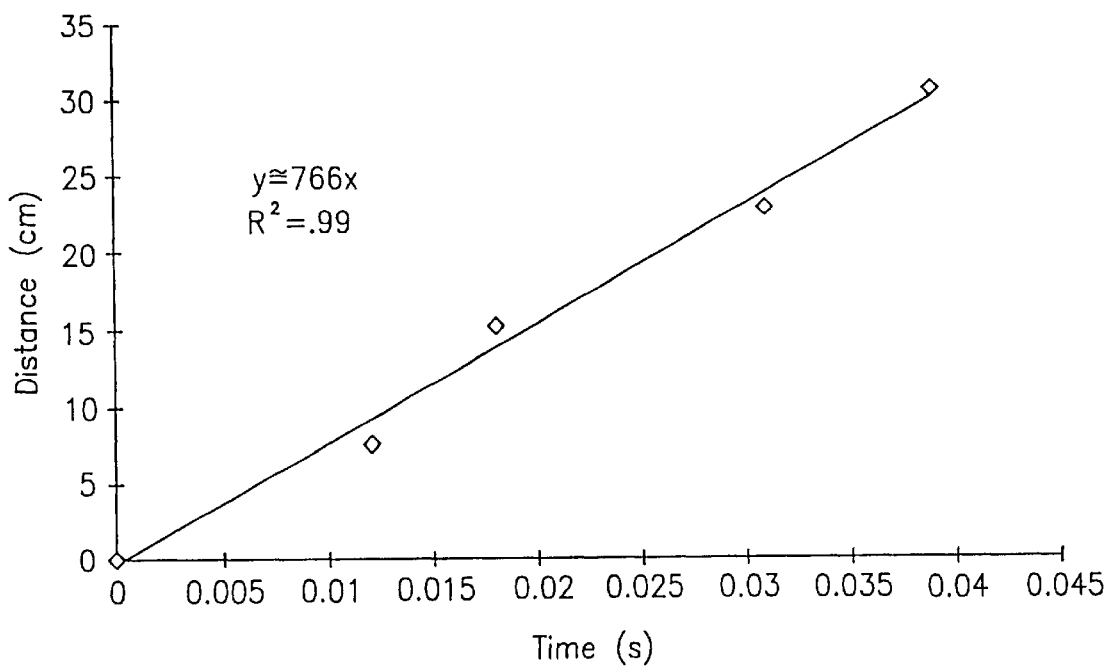
FIGS. 7A and 7B are graphs showing linear regression analysis of waveform data to determine pulse wave velocity.
Figure 7B:
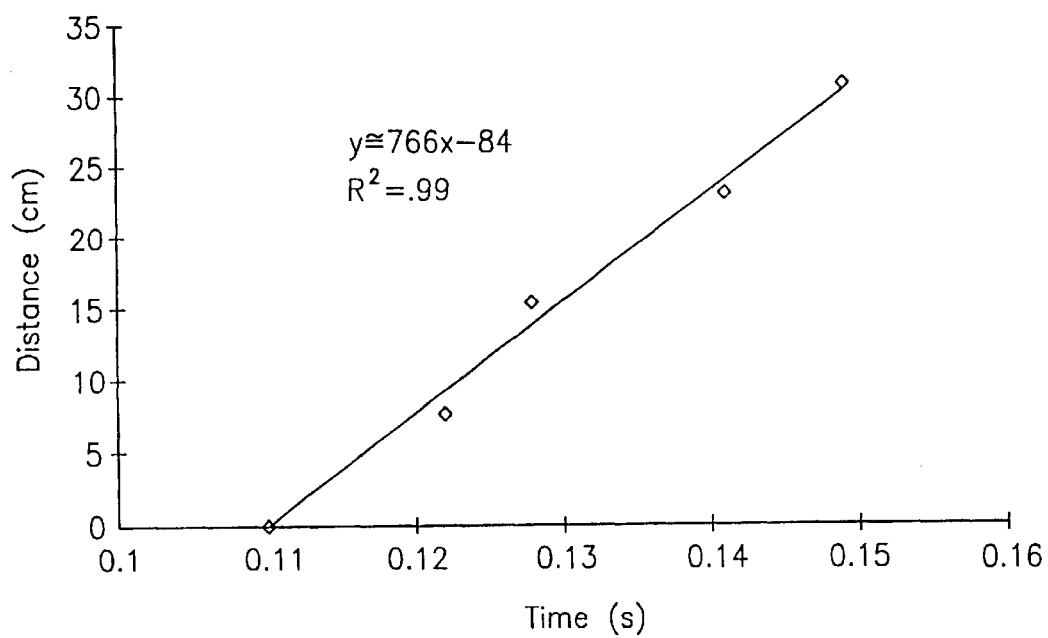

For example, FIGS. 7A and 7B show graphs of waveform data provided by five channels of PPG circuitry, e.g., five sensors with associated circuitry placed along the aorta or other blood vessel, for purposes of calculating PWV by linear regression analysis. The five sensors produce five PPG waveform signals (analogous to the two signals shown in FIG. 4), each of which is delayed slightly relative to the one before. These signals can be signal-averaged to produce five waveforms, analogous to the two waveforms shown in FIG. 5. The relative delays from a fiducial point to each of the channels (or from any one channel to each of the other channels) can then be assessed, and the location of the sensors is known (a first sensor is at 0 cm, a second sensor is at 2.5 cm, a third sensor is at 5.0 cm, etc.).

Linear regression of location vs. time delay at each of the sensors produces a line. The slope of this line is pulse wave velocity (i.e., distance over time), and the correlation coefficient R is a measure of the goodness of fit of the data to the line. Sample plots are shown in FIGS. 7A and 7B.

FIG. 7A is an example of using the first sensor as the fiducial point. Thus, the distance and time delay are both zero at the first point. Obviously, any other sensor could be used as the reference (fiducial) point.

In FIG. 7B, the QRS of the ECG waveform is used as a fiducial point. Thus, the delays are all increased by a fixed amount due to the pre-ejection period and propagation delays in the segment of aorta proximal to the first sensor. The distances are the same, since relative separation is all that is important. Note that the slope of the line in FIG. 7B (PWV=766 cm/s) is identical to the PWV in FIG. 7A. Also, as can be seen, if one sensor is detecting contaminated data, its data point will fall off of the regression line and could be readily excluded, followed by recalculation of the regression.

Whereas the above set forth description generally applies to a digital implementation of the invention, one of ordinary skill in the art will appreciate that the PWV measuring device 20 could be implemented using suitable analog circuitry without departing from the spirit and scope of the invention.

As an enhancement to the preferred embodiment of the device 20, it is possible to add a means whereby the pressure dependence of pulse wave velocity may be assessed. To this end, as shown in FIG. 2, it is possible to add a pressure transduction circuit 60 to the device 20 and to attach this to a mouthpiece pressure transducer 62 in order to measure inspiratory and expiratory force exerted by the patient during the procedure, simulating conditions of the so called Mueller and Valsalva maneuvers, respectively. The respiratory forces are transmitted to the segment of aorta 32 under study and have the effect of increasing or decreasing the effective transmural pressure acting on the aortic wall by an amount equivalent to the change in inspiratory or expiratory effort, respectively. By performing an analysis of pulse wave velocity at baseline and during graded inspiratory and expiratory effort, e.g., at ±10 mmHg, ±20 mmHg, ±40 mmHg, it is possible to evaluate the pressure dependence of pulse wave velocity over a wide range of effective mean arterial pressures.

Pulse wave velocity is first measured with the patient at rest and breathing quietly. Next, waveform data is acquired during ten seconds of −10 mmHg inspiratory force (simulating the Mueller maneuver). This is followed by ten seconds of −20 mmHg inspiratory force. Next this procedure is repeated at +10 and +20 mmHg expiratory force (simulating the Valsalva maneuver) in a similar manner. In order to ensure that inspiratory and expiratory forces are derived from the thorax and abdomen, as opposed to the nasopharynx and mouth, it is necessary to provide for a controlled air leak from the mouthpiece assembly through an appropriate resistance. The resistance is selected to ensure that approximately 200 cubic centimeters of air will escape or enter during the ten second period at each pressure level. This will prevent the patient from raising or lowering mouthpiece pressure through manipulation of the muscles of the mouth and nasopharynx alone against a closed glottis since the air capacity of the upper airway will be rapidly depleted (expiration) or exceeded (inspiration).

In order to ensure that the patient holds the air pressure at the appropriate level during each phase of the test of the pressure dependence of pulse wave velocity, it is necessary to provide visual or auditory feedback to the patient, indicating the level of airway pressure. Such feedback may be provided by displaying a pressure scale on the computer display 46 or by modulating the pitch of an emitted sound such that the frequency of the sound is proportional to the pressure being exerted on the mouthpiece. The patient could be instructed to exhale or inhale into the mouthpiece until a low frequency pitch is heard and to hold that pressure, avoiding a transition to a higher frequency pitch (too much effort) or to loss of any sound at all (too little effort).

Once data has been obtained, validated and analyzed at each inspiratory and expiratory level, it is possible to assess pressure dependence of pulse wave velocity by plotting pulse wave velocity against effective distending pressure. To assess the effective distending pressure, a blood pressure ($P_{actual}$) is first obtained from the patient just prior to the initial measurement of baseline, unstressed pulse wave velocity. Effective distending pressure ($P_{effective}$) during each phase of the evaluation of pressure dependence is obtained by subtracting the value for respiratory pressure ($P_{resp}$) during that phase of the test:

$$P_{effective} = P_{actual} - P_{resp} \qquad \text{Eq. 2.}$$

As an example, if mean arterial pressure is 90 mmHg at baseline, the effective distending pressure would be 90−(−20)=110 mmHg during −20 mmHg of inspiratory force and would be 90−(+20)=70 mmHg during +20 mmHg of expiratory force. Modeling the relationship between pulse wave velocity and effective distending pressure then provides an assessment of the pressure dependence of pulse wave velocity. This is a nonlinear, concave-upwards relationship that may be reasonably well modeled, using standard regression analysis techniques, by a quadratic equation of the form:

$$PWV_i = A + B*P_i + C*P_i^2 \qquad \text{Eq. 3.}$$

In this equation, PWV is the expected PWV at a given effective distending pressure, $P_i$. The values for A, B and C are determined by the regression analysis. Results may then be presented as a standardized PWV, e.g., the predicted PWV at a pressure of 90 mmHg. This allows for comparison of PWV values in a patient independent of blood pressure at the time of the measurement.

The above-described method of assessing the pressure dependence of pulse wave velocity provides an additional benefit of the system. Once the system has been calibrated with respect to the pressure dependence of pulse wave velocity and baseline blood pressure, it is possible to continuously monitor changes in blood pressure. As should be appreciated, the above relationship can be used to establish the expected pulse wave velocity at any given pressure or it can conversely be used to predict the current blood pressure at any given pulse wave velocity. As an example of the potential use of such a device, a patient undergoing a procedure could have a preliminary measurement of the pressure dependence of pulse wave velocity. Changes in pulse wave velocity thereafter could be used as a continuous indication of changes in pressure without the need for invasive pressure monitoring or continual inflation and deflation of a blood pressure cuff.

As can be seen by those experienced in the art, the principles outlined above for assessing pressure dependence of pulse wave velocity may be applied to any arterial segment wherein manipulation of the effective distending pressure of the vessel is possible. As an example, it would be straightforward to design a blood pressure cuff with PPG probes at the proximal (upstream with respect to arterial blood flow) and distal ends. Such a system would allow for an evaluation of the basal pulse wave velocity in the segment of brachial artery underlying the cuff. Next, the pressure-dependence of pulse wave velocity may be assessed by taking additional measurements at cuff pressures of 10, 20, 30 mmHg, etc., up to the level of the diastolic pressure. It is important to recognize that cuff pressure may not exceed diastolic pressure during this phase of the test as this will lead to collapse of the artery during late diastole and early systole and will therefore dramatically increase the apparent transit time between the probes. This data would then be processed as above except that $P_{cuff}$ would be substituted for $P_{resp}$ in Eq. 2. Once calibrated, changes in PWV could be used as an indicator of changes in blood pressure. A limit could be set for allowable levels of PWV for a given patient. If PWV moved outside these limits, the device could trigger a repeat acquisition of blood pressure to confirm the amount of change in blood pressure and could sound an alarm.

As a further enhancement to the preferred embodiment of the device 20, it is possible to add a warming means 64 for warming the skin surrounding the probe in order to produce vasodilatation, which will increase blood flow to the skin and surrounding tissues. Enhanced blood flow will improve the amplitude and quality of the signal detected by the PPG probes 22, 24. Any number of means may be used to produce such a warming effect. As an example, a pre-warmed solution could be circulated through small bladders overlying the PPG probes 22, 24. Alternatively, resistive coil-containing pads such as those employed in a standard heating pad could be placed over the probe and used to heat the skin and tissue. The coil could be deactivated at the moment of actual measurement of PPG signals in order to avoid artifacts from any induced electromagnetic field.

As should be appreciated by those with ordinary skill in the art of ambulatory monitoring, the current invention may be readily adapted to ambulatory monitoring. As noted above, pulse wave velocity is dependent upon blood pressure at the time of measurement. Thus, high pulse wave velocity may be a result of increased intrinsic stiffness of the arterial wall or increased distending pressure. In combination with ambulatory blood pressure monitoring, the present invention would provide an opportunity to evaluate changes in aortic stiffness in relationship to and independent from changes in blood pressure. Alternatively, changes in pulse wave velocity could be assessed as a measure of changes in blood pressure in a system with no direct blood pressure monitoring capability.

In a second preferred embodiment of the invention, impedance plethysmography (IPG) can be used instead of PPG. IPG electrode (transducer) placement would be similar, although a lack of dependence on the geometry of the intercostal and lumbar arteries would allow for placement of electrodes further down into the lumbar region and would allow for placement of electrodes at other sites on the body, such as the femoral, brachial or radial arteries, among others. Analysis of the data would be similar to that employed in the first preferred embodiment.

Although the device and algorithms of the present invention have been illustrated as requiring the distance between the PPG (or other) probes to be entered into a computer manually, one of ordinary skill in the art will appreciate that the distance could be calculated or determined automatically via, e.g., ultrasound or RF means provided in the probes.

As should be appreciated by those of ordinary skill in the art, all of the electronic components (computer, transducers, amplifiers, etc.) used in the present invention are standard, off-the-shelf items. As such, because many different specific components could be easily selected and used, further detail is not provided herein. Additionally, programming the computer to perform its signal processing tasks, as described above, is well within the skill of those of ordinary skill in the programming arts, and, as such, further detail is not provided herein.

Although the calculations of the pulse waveform feet have been illustrated according to the particular algorithm described herein, one of ordinary skill in the art will appreciate that different algorithms, or a modified algorithm, could be used instead without departing from the spirit and scope of the invention. For example, the preliminary and final thresholds could have values other than 50% and 20%, respectively.

Also, although the present invention has been illustrated as detecting the feet of the pulse waveforms for purposes of calculating a time difference, one of ordinary skill in the art will appreciate that other points on the pulse waveforms could be used instead without departing from the spirit and scope of the invention.

Since certain changes may be made in the above described pulse wave velocity measuring device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Having thus described the invention, what is claimed is:
What is claimed is:

1. A method for determining the pulse wave velocity of blood in the descending thoracic aorta comprising the steps of:
   a. obtaining a first pulse waveform of blood in blood vessels near a first location on the surface of a patient's skin and proximate the fourth thoracic vertebra;
   b. obtaining a second pulse waveform of blood in blood vessels near a second location on the surface of the skin and proximate the second lumbar vertebra; and
   c. calculating a pulse wave velocity by:
      i. determining a first reference point on the first pulse waveform;
      ii. using a fiducial reference point to determine a corresponding second reference point on the second pulse waveform;
      iii. determining a time difference between the first and second reference points; and
      iv. dividing a distance between the first and second surface locations by the time difference.

2. A method for determining the pulse wave velocity of blood in a blood vessel having a substantially uniform and symmetric distribution of branching blood vessels, the method comprising the steps of:
   a. obtaining a first pulse waveform of blood in blood vessels proximate a first location on the surface of a patient's skin and associated with a first location along the blood vessel;
   b. obtaining a second pulse waveform of blood in blood vessels proximate a second location on the surface of the skin and associated with a second location along the blood vessel;
   c. calculating a pulse wave velocity by:
      i. determining a foot of the first pulse waveform;
      ii. determining a foot of the second pulse waveform;
      iii. determining a time difference between the foot of the first pulse waveform and the foot of the second pulse waveform; and
      iv. dividing a distance between the first and second surface locations by the time difference
   d. repeating steps a–c to calculate a plurality of pulse wave velocities;
   e. excluding any pulse wave velocities that fall without a predetermined percentage of a mean pulse wave velocity; and
   f. averaging the remaining pulse wave velocities.

3. A method for determining pulse wave velocity in a blood vessel having a substantially uniform and symmetric distribution of branching blood vessels, the method comprising the steps of:
   a. obtaining a first pulse waveform of blood in blood vessels proximate a first location on the surface of a patient's skin and associated with a first location along the blood vessel;
   b. obtaining a second pulse waveform of blood in blood vessels proximate a second location on the surface of the skin and associated with a second location along the blood vessel;
   c. separately signal averaging the first and second pulse waveforms, wherein one of the pulse waveforms is used to provide at least one fiducial point for signal averaging the pulse waveforms; and
   d. calculating a pulse wave velocity by:
      i. determining a foot of the first pulse waveform;
      ii. determining a foot of the second pulse waveform;
      iii. determining a time difference between the foot of the first pulse waveform and the foot of the second pulse waveform; and
      iv. dividing a distance between the first and second surface locations by the time difference.

4. A method for determining pulse wave velocity in a blood vessel having a substantially uniform and symmetric distribution of branching blood vessels, the method comprising the steps of:
   a. obtaining a first pulse waveform of blood in blood vessels proximate a first location on the surface of a patient's skin and associated with a first location along the blood vessel;
   b. obtaining a second pulse waveform of blood in blood vessels proximate a second location on the surface of the skin and associated with a second location along the blood vessel; and
   c. calculating a pulse wave velocity by:
      i. determining a foot of the first pulse waveform;
      ii. determining a foot of the second pulse waveform;
      iii. determining a time difference between the foot of the first pulse waveform and the foot of the second pulse waveform; and
      iv. dividing a distance between the first and second surface locations by the time difference;
   d. wherein the step of determining each foot of the pulse waveforms comprises the sub-steps of:
      i. calculating a derivative of the pulse wave signal;
      ii. determining a peak of the derivative;
      iii. determining a first threshold value of the derivative;
      iv. determining a second threshold value of the derivative less than the first threshold value;
      v. searching forward in time from a fiducial point to determine a first point on the derivative that is the first to exceed the first threshold; and
      vi. searching back in time along the derivative to determine a second point on the derivative that is the first to exceed the second threshold, wherein the second point on the derivative is the foot of the pulse waveform.

5. The method of claim 4 further comprising the steps of: obtaining an ECG waveform; and determining a peak of a QRS portion of the ECG waveform for use as the fiducial point.

6. The method of claim 4 wherein the fiducial point is the peak of the derivative.

7. The method of claim 4 wherein:
   a. the first threshold value is equal to 50% of the peak of the derivative; and
   b. the second threshold value is equal to 20% of the peak of the derivative.

8. A device for measuring pulse wave velocity in a blood vessel having a substantially uniform and symmetric distribution of branching blood vessels, the device comprising:
   a. a signal analyzing means for analyzing signals; and
   b. first and second transducers operably electrically connected to the signal analyzing means, wherein the transducers are configured to respectively provide to the signal analyzing means first and second pulse wave signals corresponding to pulse waveforms in blood vessels proximate first and second locations on the surface of a patient's skin and associated with first and second locations along the blood vessel;
   c. wherein the signal analyzing means is configured:
      i. to record the pulse wave signals;
      ii. to display the recorded pulse wave signals and to allow a user to designate portions of the recorded pulse wave signals that are not to be used in signal averaging the pulse wave signals;
      iii. to signal average the pulse wave signals;
      iv. to use a fiducial reference point to determine a first reference point on the first pulse wave signal and a corresponding second reference point on the second pulse waveform;
      v. to determine a time difference between the first and second reference points; and
      vi. to calculate the pulse wave velocity by dividing a distance between the first and second surface locations by the time difference.

9. A device for measuring pulse wave velocity in a blood vessel having a substantially uniform and symmetric distribution of branching blood vessels, the device comprising:
   a. a signal analyzing means for analyzing signals; and
   b. first and second transducers operably electrically connected to the signal analyzing means, wherein the transducers are configured to respectively provide to the signal analyzing means first and second pulse wave signals corresponding to pulse waveforms in blood vessels proximate first and second locations on the surface of a patient's skin and associated with first and second locations along the blood vessel;
   c. wherein the signal analyzing means is configured:
      i. to use a fiducial reference point to determine a foot of the first pulse wave signal and a corresponding foot of the second pulse waveform, wherein for determining the foot of each pulse wave signal, the signal analyzing means is configured:
         A. to calculate a derivative of the pulse wave signal;
         B. to determine a peak of the derivative;
         C. to determine a first threshold value for the derivative equal to 50% of its peak;
         D. to determine a second threshold value for the derivative equal to 20% of its peak;
         E. to determine a first point on the derivative forward in time from a fiducial point that is the first to exceed the first threshold; and,
         F. searching back in time along the derivative, to determine a second point on the derivative that is the first to exceed the second threshold, wherein the second point on the derivative is the foot of the pulse wave signal;
      ii. to determine a time difference between the first and second reference points; and
      iii. to calculate the pulse wave velocity by dividing a distance between the first and second surface locations by the time difference.

10. A device for measuring pulse wave velocity in a blood vessel having a substantially uniform and symmetric distribution of branching blood vessels, the device comprising:
    a. a signal analyzing means for analyzing signals;
    b. first and second transducers operably electrically connected to the signal analyzing means, wherein the transducers are configured to respectively provide to the signal analyzing means first and second pulse wave signals corresponding to pulse waveforms in blood vessels proximate first and second locations on the surface of a patient's skin and associated with first and second locations along the blood vessel; and
    c. an ECG recording device operably electrically connected to the signal analyzing means and configured to provide to the signal analyzing means an ECG signal corresponding to a patient's ECG;
    d. wherein the signal analyzing means is configured:
       i. to determine a peak of a QRS of the ECG signal;
       ii. to record and signal average the pulse wave signals, using the QRS peak as a first fiducial point,
       iii. to use a second fiducial reference point to determine a first reference point on the first pulse wave signal and a corresponding second reference point on the second pulse waveform;
       iv. to determine a time difference between the first and second reference points; and
       v. to calculate the pulse wave velocity by dividing a distance between the first and second surface locations by the time difference.

11. The device of claim 9 wherein the signal analyzing means is configured to use the peak of the QRS as the second fiducial point in determining the reference point on each pulse wave signal.

12. A method for determining pulse wave velocity in a blood vessel having a substantially uniform and symmetric distribution of branching blood vessels, the method comprising the steps of:
    a. obtaining a first pulse waveform of blood in blood vessels proximate a first location on the surface of a patient's skin and associated with a first location along the blood vessel;
    b. obtaining a second pulse waveform of blood in blood vessels proximate a second location on the surface of the skin and associated with a second location along the blood vessel;
    c. calculating a pulse wave velocity by:
       i. determining a first reference point on the first pulse waveform;
       ii. determining a corresponding second reference point on the second pulse waveform;
       iii. determining a time difference between the first and second reference points; and
       iv. dividing a distance between the first and second surface locations by the time difference;
    d. repeating steps a–c to calculate a plurality of pulse wave velocities;

e. excluding any pulse wave velocities that fall without a predetermined percentage of a mean pulse wave velocity; and f. averaging the remaining pulse wave velocities.

13. A method for determining pulse wave velocity in a blood vessel having a substantially uniform and symmetric distribution of branching blood vessels, the method comprising the steps of:

a. obtaining a first pulse waveform of blood in blood vessels proximate a first location on the surface of a patient's skin and associated with a first location along the blood vessel;

b. obtaining a second pulse waveform of blood in blood vessels proximate a second location on the surface of the skin and associated with a second location along the blood vessel; and c. calculating a pulse wave velocity by:
 i. determining a first reference point on the first pulse waveform;
 ii. determining a corresponding second reference point on the second pulse waveform;
 iii. determining a time difference between the first and second reference points; and
 iv. dividing a distance between the first and second surface locations by the time difference;

d. wherein the steps of determining the first and second reference points on the pulse waveforms each comprise the sub-steps of:
 i. calculating a derivative of the pulse wave signal;
 ii. determining a peak of the derivative;
 iii. determining a threshold value of the peak of the derivative; and
 iv. searching along the derivative to determine a point on the derivative at the threshold value, wherein that point is the reference point on the pulse waveform.

14. A method for determining pulse wave velocity in a blood vessel comprising the steps of:

a. obtaining a pulse waveform of blood in blood vessels proximate each of a plurality of spaced-apart locations on the surface of the skin and associated with a plurality of spaced-apart locations along the blood vessel;

b. using a fiducial reference point, determining corresponding reference points on the pulse waveforms; and c. applying linear regression analysis to the corresponding reference points on the pulse waveforms to determine pulse wave velocity.

15. The method of claim 14 wherein the reference point on each pulse waveform is the foot of the pulse waveform, as determined in each case by:

a. calculating a derivative of the pulse waveform;

b. determining a peak of the derivative;

c. determining at least one threshold value of the peak of the derivative; and d. searching along the derivative to determine a point on the derivative at the threshold value, wherein that point is foot of the pulse wave signal.

16. The method of claim 14 wherein the reference point on each pulse waveform is the foot of the pulse waveform, as determined in each case by:

a. calculating a derivative of the pulse waveform;

b. determining a peak of the derivative;

c. determining a first threshold value of the derivative;

d. determining a second threshold value of the derivative less than the first threshold value;

e. searching forward in time from a fiducial point to determine a first point on the derivative that is the first to exceed the first threshold; and f. searching back in time along the derivative to determine a second point on the derivative that is the first to exceed the second threshold, wherein the second point on the derivative is the foot of the pulse waveform.

17. The method of claim 14 wherein the method further comprises the step of separately signal averaging the pulse waveforms, wherein one of the pulse waveforms is used to provide at least one fiducial point for signal averaging the pulse waveforms.

18. The method of claim 17 wherein the pulse waveforms are screened for extraneous noise content and waveform shape, and the highest quality pulse waveform is used to provide the at least one fiducial point for signal averaging the pulse waveforms.

19. The method of claim 14 wherein the step of applying linear regression analysis is performed with respect to a fiducial point provided by one of the pulse waveforms.

20. The method of claim 14 wherein the step of applying linear regression analysis is performed with respect to a fiducial point provided by a recorded ECG waveform.

21. A method for determining pulse wave velocity in a blood vessel comprising the steps of:

a. obtaining a pulse waveform of blood in blood vessels proximate each of at least three spaced-apart locations on the surface of the skin and associated with at least three spaced-apart locations along the blood vessel;

b. using a fiducial reference point, determining corresponding reference points on the pulse waveforms and the relative time delays from the fiducial reference point to the corresponding reference points; and c. using linear regression analysis to calculate pulse wave velocity, wherein the slope of a generally linear relationship between the corresponding reference points, each as a function of respective location on the surface of the skin versus relative time delay, is the pulse wave velocity.

22. The method of claim 21 further comprising the steps of:

a. determining if any of the corresponding reference points, as a function of respective location on the surface of the skin versus relative time delay, fall substantially outside the linear relationship; and b. recalculating pulse wave velocity without the corresponding reference points that fall substantially outside the linear relationship.

23. A method for determining pulse wave velocity in a blood vessel comprising the steps of:

a. obtaining a pulse waveform of blood in blood vessels proximate each of a plurality of spaced-apart locations on the surface of the skin and associated with a plurality of spaced-apart locations along the blood vessel;

b. separately signal averaging the pulse waveforms, wherein one of the pulse waveforms is used to provide at least one first fiducial point for signal averaging the pulse waveforms; and c. calculating a pulse wave velocity by:
 i. determining corresponding reference points on the pulse waveforms, wherein each corresponding reference point has an associated time point; and
 ii. determining a generally linear relationship between the time points and the spaced-apart locations on the surface of the skin, wherein the generally linear relationship is the pulse wave velocity.

24. The method of claim 23 wherein the step of determining the generally linear relationship comprises the substeps of determining the time differences between the corresponding reference points; and dividing the distances between the spaced-apart locations on the surface of the skin by respective time differences.

25. The method of claim 23 wherein the step of determining the generally linear relationship comprises using linear regression analysis to calculate pulse wave velocity, wherein the slope of the generally linear relationship between the corresponding reference points, each as a function of respective location on the surface of the skin versus relative time delay, is the pulse wave velocity.

26. The method of claim 23 wherein the pulse waveforms are screened for extraneous noise content and waveform shape, and the highest quality pulse waveform is used to provide the at least one first fiducial point for signal averaging the pulse waveforms.

27. The method of claim 23 wherein one of the pulse waveforms is also used to provide at least one second fiducial point for determining the corresponding reference points on the pulse waveforms.

28. A method for determining pulse wave velocity in a blood vessel comprising the steps of:
  a. obtaining pulse waveforms at least three spaced-apart locations along the blood vessel;
  b. using a fiducial reference point, determining corresponding reference points on the pulse waveforms; and
  c. applying linear regression analysis to the corresponding reference points on the pulse waveforms to determine pulse wave velocity.

29. The method of claim 28 further comprising the step of separately signal averaging the pulse waveforms using at least one fiducial provided by one of the pulse waveforms.

30. A device for measuring pulse wave velocity in a blood vessel comprising:
  a. a signal analyzer; and
  b. at least three transducers operably electrically connected to the signal analyzer, wherein the transducers are configured to provide to the signal analyzer respective pulse wave signals corresponding to pulse waveforms in blood vessels proximate a plurality of spaced-apart locations on the surface of the skin and associated with at least three spaced-apart locations along the blood vessel;
  c. wherein the signal analyzer is configured:
    i. to record the pulse wave signals;
    ii. using a fiducial reference point, to determine corresponding reference points on the pulse wave signals and the relative time delays from the fiducial reference point to the corresponding reference points; and
    iii. to calculate pulse wave velocity using linear regression analysis, wherein the slope of a generally linear relationship between the corresponding reference points, each as a function of respective location on the surface of the skin versus relative time delay, is the pulse wave velocity.

31. A device for measuring pulse wave velocity in a blood vessel comprising:
  a. a signal analyzer; and
  b. a plurality of transducers operably electrically connected to the signal analyzer, wherein the transducers are configured to provide to the signal analyzer respective pulse wave signals corresponding to pulse waveforms in blood vessels proximate a plurality of spaced-apart locations on the surface of the skin and associated with a plurality of spaced-apart locations along the blood vessel;
  c. wherein the signal analyzer is configured:
    i. to record the pulse wave signals;
    ii. to separately signal average the pulse wave signals, with one of the pulse wave signals being used to provide at least one first fiducial point for signal averaging the pulse wave signals; and
    iii. to calculate a pulse wave velocity by: determining corresponding reference points on the pulse wave signals, wherein each corresponding reference point has an associated time point; and determining a generally linear relationship between the time points and the spaced-apart locations on the surface of the skin, wherein the generally linear relationship is the pulse wave velocity.

* * * * *

UNITED STATES PATENT AND TRADEMARK OFFICE
CERTIFICATE OF CORRECTION

PATENT NO. : 6,331,162 B1
DATED : December 18, 2001
INVENTOR(S) : Gary F. Mitchell It is certified that error appears in the above-identified patent and that said Letters Patent is hereby corrected as shown below:

Column 9,
Line 37, change "In this equation, PWV" to -- In this equation, PWV; --.

Column 11,
Line 30, delete "What is claimed is:".

Please add Claim 32:
    32.    A method for determining the pulse wave velocity of blood in the descending thoracic aorta comprising the steps of:

a.    obtaining a first pulse waveform of blood in blood vessels near a first location on the surface of a patient's skin and proximate the fourth thoracic vertebra;

b.    obtaining a second pulse waveform of blood in blood vessels near a second location on the surface of the skin and proximate the second lumbar vertebra; and
    c.    calculating a pulse wave velocity by:
        i.    determining a foot of the first pulse waveform;
        ii.    determining a foot of the second pulse waveform;
        iii.    determining a time difference between the foot of the first pulse waveform and the foot of the second pulse waveform; and
        iv.    dividing a distance between the first and second surface locations by the time difference.

Column 17,
Line 43, change "a plurality of" to -- at least three --.

Signed and Sealed this

Twenty-third Day of April, 2002

*Attest:*

*Attesting Officer*

JAMES E. ROGAN
*Director of the United States Patent and Trademark Office*